(12) United States Patent
Vincent

(10) Patent No.: US 10,201,450 B2
(45) Date of Patent: Feb. 12, 2019

(54) INTRABUCCAL DEVICE COMPRISING BITE TRAYS AND CONNECTING RODS

(71) Applicant: ONIRIS, Chaville (FR)

(72) Inventor: Thibault Vincent, Rueil Malmaison (FR)

(73) Assignee: ONIRIS (FR)

( * ) Notice: Subject to any disclaimer, the term of this patent is extended or adjusted under 35 U.S.C. 154(b) by 208 days.

(21) Appl. No.: 14/416,991

(22) PCT Filed: Jul. 17, 2013

(86) PCT No.: PCT/FR2013/051726
§ 371 (c)(1),
(2) Date: Jan. 23, 2015

(87) PCT Pub. No.: WO2014/016495
PCT Pub. Date: Jan. 30, 2014

(65) Prior Publication Data
US 2015/0202075 A1    Jul. 23, 2015

(30) Foreign Application Priority Data

Jul. 24, 2012  (FR) ...................................... 12 57158

(51) Int. Cl.
| | |
|---|---|
| *A61F 5/56* | (2006.01) |
| *A61C 7/08* | (2006.01) |
| *A61C 7/36* | (2006.01) |

(52) U.S. Cl.
CPC ................ *A61F 5/566* (2013.01); *A61C 7/08* (2013.01); *A61C 7/36* (2013.01)

(58) Field of Classification Search
CPC .... A61C 7/08; A61C 7/36; A61C 7/06; A61C 7/10; A61C 7/12; A61C 5/14; A61F 5/56; A61F 5/566; A61F 5/0006; A61F 2005/563; A63B 71/085; A63B 71/086; A63B 71/087; A63B 71/088
USPC ........ 128/848, 859, 861, 862, 846; 433/5, 6, 433/7, 8, 19, 24, 140, 2, 11, 37, 34, 433/41–44
See application file for complete search history.

(56) References Cited

U.S. PATENT DOCUMENTS

| | | | |
|---|---|---|---|
| 5,120,218 A | | 6/1992 | Hanson |
| 5,620,321 A | * | 4/1997 | Thornburg ................ A61C 7/36 |
| | | | 433/19 |
| 6,109,265 A | * | 8/2000 | Frantz ..................... A61F 5/566 |
| | | | 128/848 |

(Continued)

FOREIGN PATENT DOCUMENTS

| | | |
|---|---|---|
| DE | 20 2008 011 841 U1 | 11/2008 |
| EP | 2 143 397 | 1/2010 |

(Continued)

OTHER PUBLICATIONS

English Translation—EP 2143397 A1—Vincent Gerard (Jan. 2010).*

(Continued)

*Primary Examiner* — Ophelia A Hawthorne
(74) *Attorney, Agent, or Firm* — Ostrolenk Faber LLP

(57) ABSTRACT

Bite trays (10, 11) having lateral cylindrical pivots (30) articulating two connecting rods (20) in propulsion, the front fastening elements (30*a*) operate according to a transverse elastic click-lock system and the rear connecting-rod fastening elements (30*b*) operate according to an open-ring radial locking system, in order to increase the operating safety under all circumstances.

10 Claims, 2 Drawing Sheets

(56) References Cited

U.S. PATENT DOCUMENTS

| | | | | |
|---|---|---|---|---|
| 6,526,982 | B1* | 3/2003 | Strong | A61F 5/566 128/848 |
| 2003/0190575 | A1* | 10/2003 | Hilliard | A61C 7/00 433/6 |
| 2010/0006107 | A1* | 1/2010 | Arni | A61F 5/566 128/848 |
| 2011/0000495 | A1* | 1/2011 | Ash | A61F 5/566 128/848 |
| 2011/0003262 | A1* | 1/2011 | Frantz | A61C 7/36 433/2 |
| 2011/0155144 | A1* | 6/2011 | Tousssaint | A61F 5/566 128/848 |
| 2011/0311936 | A1* | 12/2011 | Marie-Catherine | A61F 5/566 433/19 |

FOREIGN PATENT DOCUMENTS

| | | | |
|---|---|---|---|
| EP | 2529710 A1 * | 12/2012 | ............ A61F 5/566 |
| FR | 2 887 135 A1 | 12/2006 | |
| FR | 2 964 853 A1 | 3/2012 | |

OTHER PUBLICATIONS

International Search Report dated Nov. 20, 2013 issued in corresponding International patent application No. PCT/FR2013/051726.

Written Opinion dated Nov. 20 2013 issued in corresponding International patent application No. PCT/FR2013/051726.

International Preliminary Report on Patentability issued in corresponding International patent application No. PCT/FR2013/051726.

* cited by examiner

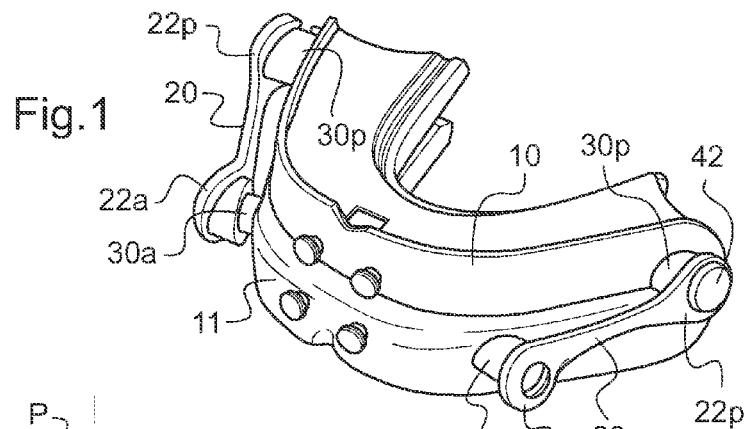
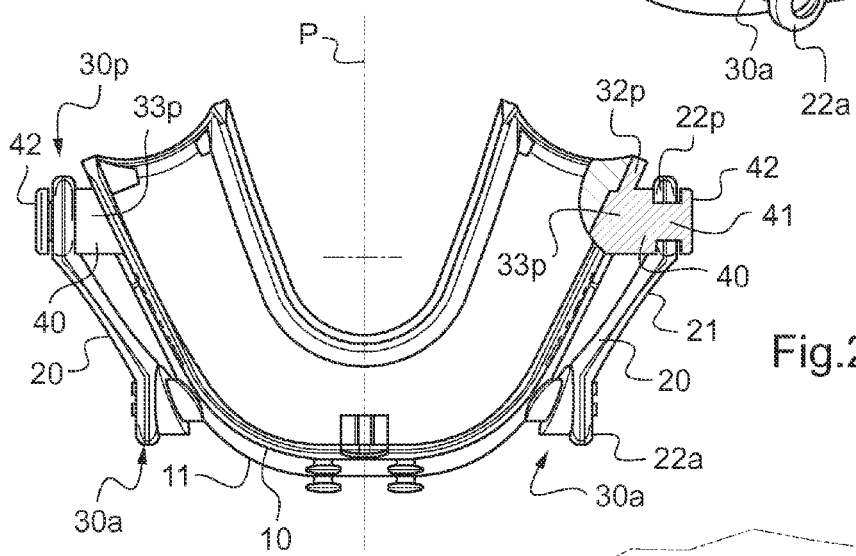
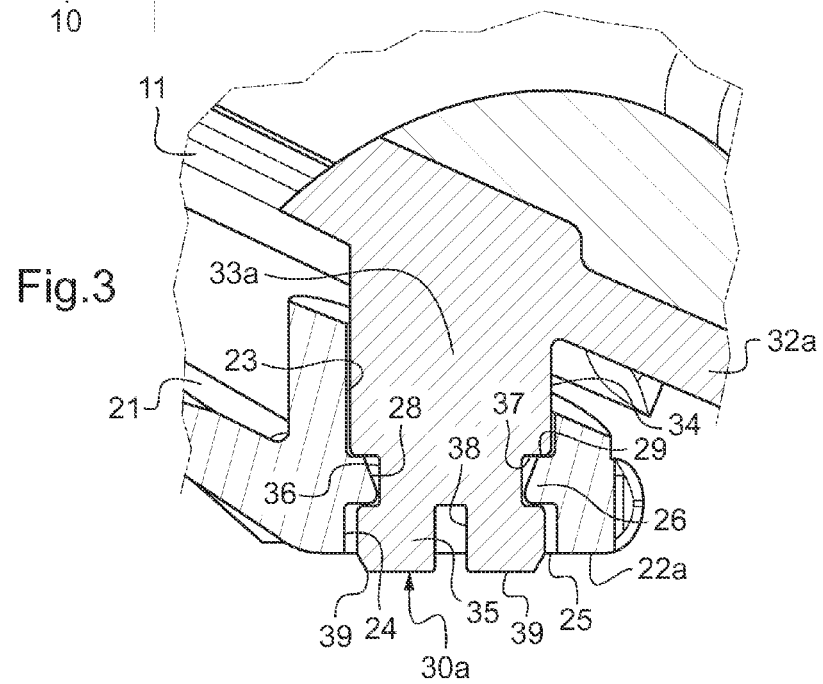

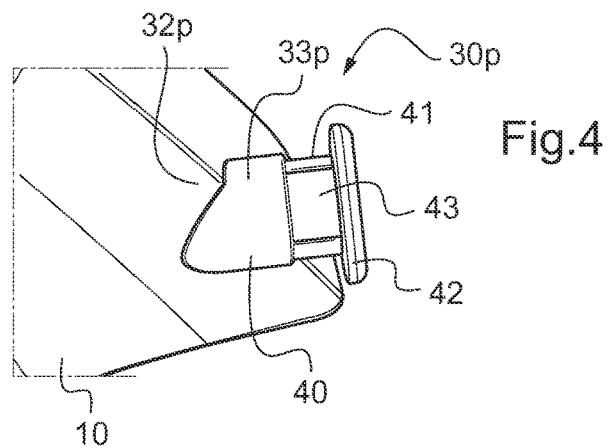
Fig.4
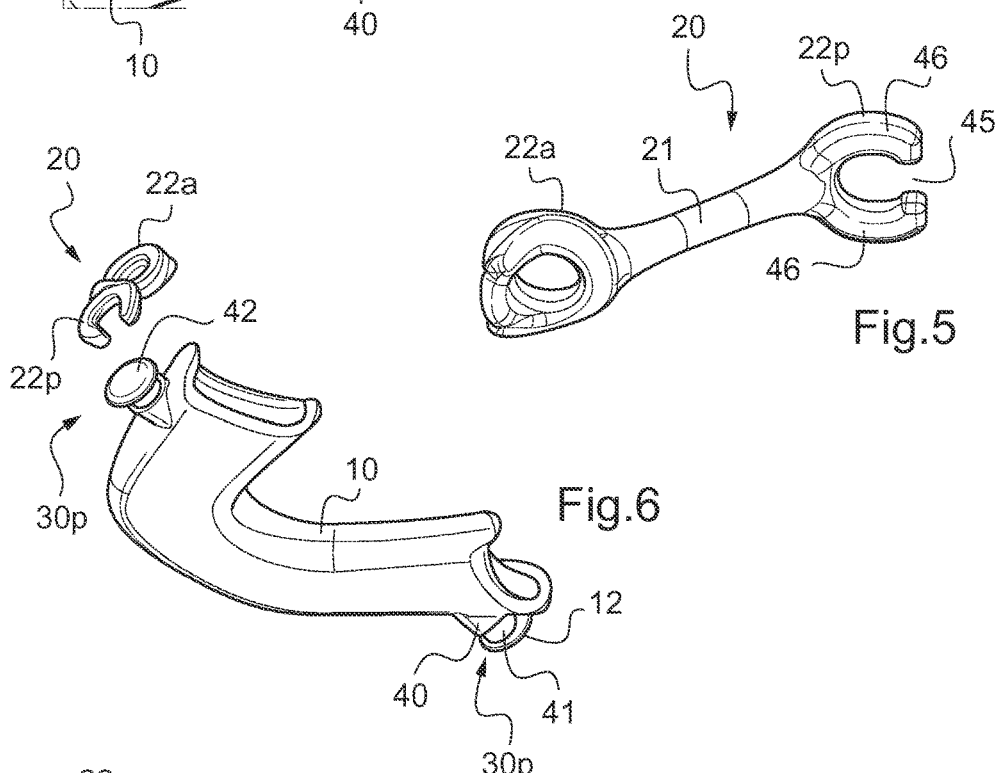
Fig.5
Fig.6
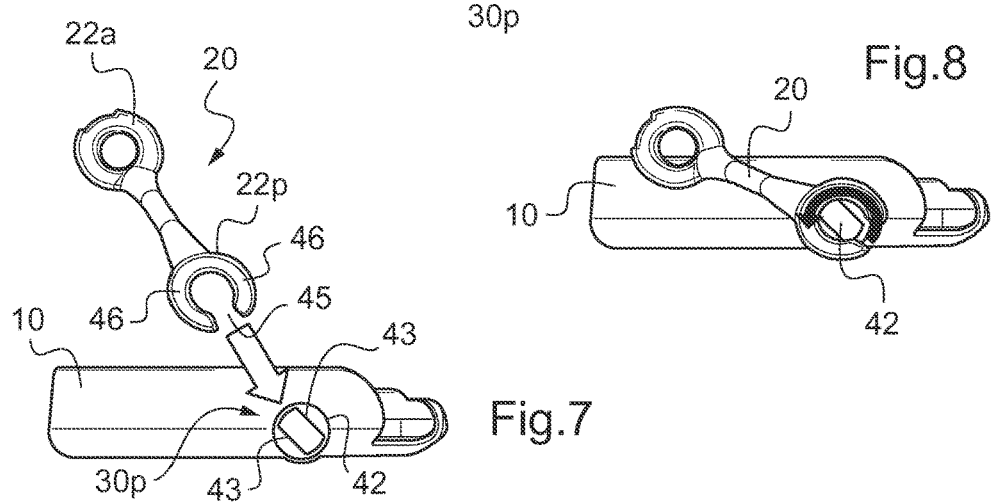
Fig.7
Fig.8

INTRABUCCAL DEVICE COMPRISING BITE TRAYS AND CONNECTING RODS

CROSS REFERENCE TO RELATED APPLICATIONS

The present application is a 35 U.S.C. § 371 National Phase conversion of PCT/FR2013/051726, filed Jul. 17, 2013, which claims benefit of French Application No. 1257158, filed Jul. 24, 2012, the disclosure of which is incorporated herein by reference. The PCT International Application was published in the French language.

TECHNICAL FIELD OF THE INVENTION

The present invention relates to an intrabuccal device having bite trays and connecting rods, the bite trays being intended to be fitted to the dental arches of the lower and upper jaws of a subject and connected by connecting rods, preferably made of plastic, fixed to fixing devices suited to these connecting rods. The connecting rods form part of a set of connecting rods of different sizes.

BACKGROUND OF THE INVENTION

Document EP 2 143 397 discloses a pair of bite trays which are connected by connecting rods having a through-orifice comprising a first cross section that is larger than the cross section of the axis of the fixing device and a second cross section corresponding to the oriented radial fingers end section of the axis. In a first position, the orifice that passes through the connecting rod lug is aligned with the two radial fingers of the pivot and can be engaged. In a second position, the two radial fingers are no longer aligned with the profiled section of the through-orifice, preventing the connecting rod from being disengaged.

In this configuration, the axis of engagement and of disengagement of the connecting rod with respect to the pivot is unique and parallel to the axis of the pivot, which is transverse to the median sagittal plane of the device; this is a means of fitting which will therefore be referred to here as transverse. Blocking in the fitted position is achieved by contact between the radial fingers of the axis and the profiled section of the connecting rod end.

This system generally proves satisfactory when the fixing device offers a great deal of mechanical strength over a very small cross section, at the radial fingers of the axis. That requires the use of parts made of metal. This configuration also leads to wearing of the profiled section of the connecting rod lug, resulting in a loss of functionality.

Also known from documents DE202008011841U1 and FR2964853 is a device having a pair of bite trays and associated connecting rods having systems better suited to be produced in molded plastic. The pair of bite trays comprises lateral pivots intended to articulate the ends of the two connecting rods that connect a pivot of one bite tray to a pivot of the other bite tray and the pivot comprises means of elastically clip-fastening connecting rod ends.

As before, in this configuration the axis of engagement and of disengagement of the connecting rod with respect to the pivot is unique and parallel to the axis of the pivot. This is an elastic clip-fastening or clipping-together that is transverse.

This system generally proves satisfactory notably when the fixing device is fitted in such a way as to move the lower jaw forward by traction. The anterior fitting is therefore situated at the upper jaw and the lower jaw is moved forward by reducing the size of the connecting rods.

The traction configuration has a major disadvantage of keeping the user's mouth closed during the propulsion. That may lead to discomfort in certain individuals and limits the possibilities of moving the jaw forward, and therefore the effectiveness of the treatment.

In addition, during sleep, mouth-opening movements are numerous, particularly in the case of snoring and sleep apnea. When the opening force is greater than the retention of the bite trays on the teeth, that causes the bite trays to disengage and makes the treatment ineffective.

A propulsion system, on the other hand, offers the advantage of allowing the mouth to be opened. The anterior fixings are therefore positioned on the lower bite tray and the forward movement is performed by lengthening the connecting rods, as disclosed in document FR2964853.

In such a propulsion system, the connecting rods are subjected to compression under the effect of the return forces exerted by the lower jaw. In this configuration, the force transmitted by the connecting rod has a component the axis of which is separate from the axis of symmetry of the patient and the direction of which is oriented toward the outside of the jaw; this component directed toward the outside of the pivot may cause the connecting rod to disengage, particularly in subjects that suffer from bruxism.

It has therefore become apparent that it is desirable to improve the known device in order to obtain a system that is particularly well suited to being made in molded plastic for a forward movement by propulsion. That is the object of the invention.

SUMMARY OF THE INVENTION

The invention achieves its objective by virtue of an intrabuccal device having a pair of bite trays and associated connecting rods, the bite trays defining a median sagittal plane, each bite tray comprising at least two anterior or posterior transverse lateral fixings intended to articulate the ends of two substantially rigid connecting rods arranged in a vestibular position and respectively laterally connecting an anterior fixing of one bite tray to a posterior fixing of the other bite tray, each fixing and each connecting rod end comprising means of pivot-mounting the one on the other with transverse blocking, two of the anterior or posterior fixings and the associated connecting rod ends comprising first means of fitting by elastic snap-fastening in a direction orthogonal to the median sagittal plane, characterized in that the other two fixings and the associated connecting rod ends comprise second means of fitting by open-ring radial locking in a plane parallel to the median sagittal plane.

A transverse lateral fixing means that the axis of articulation that it defines in collaboration with the associated connecting rod end is transverse to the median sagittal plane, and preferably orthogonal thereto.

Open-ring radial locking is the name given here to the type of pivoting fitting obtained when a male element and a female element with an open ring are made to collaborate, the male element having, in a certain orientation, a transverse dimension that is smaller than the opening of the ring and, in the other orientations, a transverse dimension that is larger than the opening of the ring so that the male element can be inserted, like a key, in a precise orientation with respect to the female element, which acts like a lock and, once it has been introduced into this female element, can turn therein but is blocked transversely as long as it does not return to the orientation in which it was introduced or another introduction orientation of the same type. The introduction radial orientation (with respect to the aforementioned axis of articulation, or in other words the orientation in a plane parallel to the median sagittal plane) is chosen to correspond to a radial position of the connecting rod with respect to the bite tray that is very different from the working position of the connecting rod once fitted (i.e. once it has been fixed to its two, anterior and posterior, pivots); when the connecting rod is in the fitted position, the open-ring locking system firmly locks the connecting rod to the fixing. The smallest transverse dimension of the male element is advantageously obtained by virtue of two diametrically opposed parallel flats formed on a generally cylindrical surface of the male element, this surface advantageously consisting of a throat formed in a pivot.

One of the advantages of the invention associated with the use of this type of connection by open-ring radial locking in a plane parallel to the sagittal plane is that it allows the lateral travel of the connecting rod to be adjusted to a large extend by adjusting the clearance of the various elements at the connection. It is possible to elect to have a certain lateral clearance, but it is also possible to elect to eliminate this clearance by tight adjustment of the connection, something which may prove to be advantageous in the case of bruxism.

As specified above, the first means of fitting with elastic clip-fastening have transverse clip-fastening, i.e. clip-fastening along the transverse axis of the fixings which, as has already been mentioned, are provided orthogonal to the median sagittal plane (i.e. in such a way as to form, for the connecting rod, an axis of pivoting orthogonal to said sagittal plane).

Advantageously, the first means of fitting are provided on the anterior fixings which are on the lower bite tray, and the second means of fitting are on the posterior fixings which are on the upper bite tray, the connecting rods thus being fitted in a propulsion set up.

The means of fitting comprise two-way transverse stop means, once fitted, for preventing the connecting rod from leaving the fitting and also for preventing it from getting too close to the bite trays.

The invention is particularly well suited to the connecting rods being made of molded semi-rigid or rigid plastic.

In a way known per se, the fixing may constitute the pivot (the male element) and it is the connecting rods which at their end comprise the female element: each connecting rod is made up of a planar central part defining an axis and of two end lugs each defining a plane, the two said planes defined by the end lugs being distinct and being parallel to the aforementioned median sagittal plane, said axis of the central part intersecting these two planes at a none-zero angle. In one particular embodiment, the posterior pivot is made up of a base contiguous with the upper bite tray, of a wide throat and of an external shoulder forming the exterior transverse stop. The connecting rod has an end with a circular profile, in a ring advantageously open over a section that is sufficient that it can be engaged over the throat of the pivot. The throat of the pivot has a cylindrical profile with two oriented parallel flats and the cross section of the open end of the connecting rod is substantially equivalent to the distance between flats. Thus, in a position parallel to the flats, the connecting rod lug can engage in the throat and in a second, radial, working (wearing) position that makes an angle (and advantageously more or less a right angle) with the planes of the flats, disengagement is impossible.

Disengagement is naturally impossible in the wearing position, i.e. the propulsion position, the return force exerted by the lower jaw placing the connecting rod under compression and keeping it engaged in the throat of the posterior pivot. However, according to the invention, it is therefore also kept engaged during commonplace use when the movement may happen to be reverse (during yawning, movement in the night, etc.) and places the connecting rod temporarily under tension; the open-ring radial locking prevents disengagement.

The device of the invention may be varied in its own mirror image, the connecting rod bearing a pivot provided with two flats and engaging in a complementary female-shaped form in the fixing of the bite tray.

Thus, within the context of a system involving plastic connecting rods, the invention succeeds in ensuring both simplicity of adjustments and effective securing in a system that moves the mandible forward by propulsion, whatever the movements performed in commonplace use.

In a way known per se, the means of elastic clip-fastening the connecting rods consist of a relief provided on a cylindrical surface of one out of the male or female elements which is provided on the fixing and intended to collaborate with a substantially complementary relief on the female or male element which is provided at the connecting rod end. In a preferred embodiment, the pivot is a male half-pin with a split end borne by one of the male or female elements and collaborates with a bushing formed in the other, female or male, element.

It can be seen that one of the features of the invention is that it has anterior and posterior ends of different nature for the connecting rods: elastic clip-fastening in the direction transverse to the median sagittal plane for the anterior end and radial locking (radial with respect to the axis of articulation which is itself transverse to the sagittal plane) with an open ring, namely locking achieved by a radial orientation for insertion of the end of the connecting rod which is in the shape of an open ring over the axis of articulation and pivoting in the radial plane (parallel to the sagittal plane) to achieve locking.

It is the combination of these two different and specific types of fitting that affords the advantages of ease of fitting and of use, robustness and comfort to the patient that are explained in the description. These means of fitting may potentially be known individually in the prior art, but not in the combination claimed in the invention. Thus, document FR 2 887 135 discloses a connecting rod which at its two ends comprises the same means of fitting rather than two different means. Moreover, document U.S. Pat. No. 5,620,321 discloses a connecting rod which does indeed at its two ends comprise means of fitting which are different but these differ from those of the invention. Firstly, the fitting of the anterior end of the connecting rod is performed by elastic clip-fastening, and still less by transverse elastic clip-fastening. Specifically, projections present on a connecting rod end fork provide only temporary retention while awaiting the next step of fitting which involves crimping the ends of the fork. Definitive fitting is therefore a crimped fitting made possible by the fact that the connecting rod end, like the connecting rod itself, is made of metal. The present invention targets connecting rods preferably made of plastic, and offers definitive fitting by elastic clip-fastening. In addition, the fitting of the posterior end of the connecting rod is also of a type very different from that of the present invention: it can be likened thereto insofar as use is made of a kind of key and of locking by rotation, but works on a different principle. The connecting rod end is introduced onto the ball while transverse to the sagittal plane and is then turned to adopt its position in the plane parallel to the sagittal plane. By contrast, according to the invention, the connecting rod is always in a plane parallel to the sagittal plane and is turned radially about the axis of articulation of the pivot. That allows for easier installation in the mouth, on the one hand, and especially, on the other hand, the principle of using a simple open-ring key system means that the connecting rod can be produced in the form of a fairly slender molded component. The posterior fitting part of the connecting rod known from the document cited is relatively easy to produce by drilling a metal component, but less so by molding a plastic component; in any event, all other things being equal, it leads to a component that is thicker and therefore more unpleasant in the mouth for the patient. In addition, the posterior fitting of the connecting rod in the form of a ball in the known document does not make it possible to eliminate the lateral play of the connecting rod, unlike the present invention, as was seen earlier.

BRIEF DESCRIPTION OF THE DRAWINGS

Other features and advantages of the invention will become apparent from the following description of some exemplary embodiments. Reference will be made to the attached drawings in which:

FIG. 1 is a diagram in perspective of the intrabuccal device of the invention, with the pair of bite trays fitted with their two connecting rods in the propulsion position.

FIG. 2 is a more detailed view from above of the pair of bite trays of FIG. 1, with a cross section with cutaway of the detail of a posterior connecting rod articulating and fitting device according to the invention, using an open ring.

FIG. 3 is a detail, in cross section, of an earlier fitting device using transverse elastic clip-fastening.

FIG. 4 is a detail of the flatted pivot of a posterior fitting device.

FIG. 5 is a perspective view of a connecting rod according to the invention.

FIGS. 6 to 8 depict three successive phases in the installing of an open-ring connecting rod end on a flatted pivot.

DESCRIPTION OF EMBODIMENTS

FIGS. 1 and 2 schematically depict the bite tray 10 of the dental arch of the upper jaw (or maxilla) situated above the bite tray 11 of the dental arch of the lower jaw (or mandible). The two dental arch bite trays 10, 11 are substantially in the shape of a U-section hollow channel and are symmetric with respect to the median sagittal plane P of the subject. The plane of extension and of contact of the bite trays, which is defined between the upper and lower bite trays, is defined as a transverse plane orthogonal to the plane P. The bite tray 11 of the lower arch is depicted here as being forward of the bite tray 10 of the upper arch. The two bite trays are intended to accommodate in their channel a thermoformable material 40 which creates an impression of the teeth, for example made of EVA (ethylene vinyl acetate).

The two dental arch bite trays 10 and 11 are connected by two connecting rods 20 each articulated at their two ends to anterior 30a and posterior 30p fixing devices connected respectively to a dental arch bite tray 10 or 11. These two fixing devices 30a, 30p are positioned as close as possible to the transverse contact plane so as to minimize the opening of the mouth during propulsion, as this would lead to a loss of effectiveness and to discomfort to the wearer. The connecting rods 20 are in a vestibular position, lateral with respect to the jaws.

Each fixing device 30a, 30p comprises a base 32a, 32p and a pivot 33a, 33p in the form of a male cylindrical half-axis. The base 32a, 32p is integrated into the profile of the shell of the bite tray 10 or 11 or is molded as an integral part thereof. The cylindrical pivot 33a, 33p, molded into the base 32a, 32p, is perpendicular to the median plane P and therefore makes an angle with the base 32a, 32p or with the surface of the bite tray 10, 11 if there is no distinct base or if the base does not have the transverse shape depicted. The pivot 33a, 33p is made of a relatively rigid and elastic thermoplastic, for example SEBS (a styrene-ethylene-butylene-styrene copolymer, possibly modified).

The two fixing devices, anterior 30a and posterior 30p, may have the pivot 33a, 33p inclined to a greater or lesser extend with respect to the surface of the bite tray 10, 11 so as to keep the pivot 33a, 33p perpendicular to the median sagittal plane P.

The two fixing devices, anterior 30a and posterior 30p, differ in how they are fitted. The anterior device 30a is of the elastic clip-fastening type of the prior art, whereas the posterior device, on the upper bite tray 10, is of the open-ring radial locking type as will be described later on.

Each connecting rod 20 (cf. also FIG. 5) consists of a substantially rigid plate, in the form of an elongate and flattened Z, advantageously obtained by molding a plastic. It comprises a main body 21, in the form of an elongate thin plate, for example measuring 1 mm or less, or in the form of a rod of more or less round cross section, at the ends of which are formed, at an angle, two anterior 22a and posterior 22p rounded lugs which via their exterior faces define distinct parallel planes which are parallel to the median plane P when the connecting rod 20 is in place. These two planes are separated by a none-zero distance, corresponding to the installation separation between the front and rear fixing devices 30. The thickness of the lugs 22a, 22b may be greater than that of the central part 21 of the connecting rod, so that the means for articulated fitting to the fixing devices 30a, 30p can be formed therein. The connecting rods are made by molding a rigid or semi-rigid plastic such as POM (polyoxymethylene) or polycarbonate.

Of course, as in the invention of document EP 2 143 397, the two connecting rods that have been shown form part of a set of several connecting rods of different lengths which are intended to suit different extends to which one jaw protrudes beyond the other, during the titration process.

The makeup of the anterior first means of attachment 30a by transverse elastic clip-fastening, shown in FIG. 3 in an advantageous embodiment, will be recalled first of all.

The lug 22a forms a female element or bushing in which the half-axis male element 33a swivels, with transverse stop elements provided to block the transverse travel of the connecting rod in the two transverse directions toward or away from the bite tray 11. To this end, the lug 22a is pierced with an orifice 25 comprising a cylindrical first section 23, on the side facing toward the bite tray 11, followed by a second section 24, on the outside, separated from the first section 23 by a circular internal rib 26. The diameter D1 of the first section 23 is just slightly greater than the diameter d1 of the first section 34 of the pivot 33a in order to leave sufficient minimal articulation clearance to allow the pivot to be introduced into the orifice in the connecting rod. The diameter D2 of the second section 24 is greater than the diameter d2 of the second section 35 of the pivot 33a, with a clearance greater than the clearance between the first pivot and lug sections. The dimensions of the rib 26 are such that the rib 26 can fit into the throat 36 of the pivot, with a minimal clearance in the direction of the axis of the pivot. The rib 26 has a frustoconical chamfered face 28 to allow it to be fitted more easily; the divergent surface 28 has its diameter decreasing with increasing distance away from the bite tray. A rounded or chamfered edge is provided at its smallest-diameter end to make pivot disengagement easier. As the orifice 25 in the lug 22a passes over the pivot 33a, the rib 26 first of all bears via its face 29 facing toward the bite tray, on the two end half-sections 39 of the pivot 33a, which are chamfered on their edge and can close up elastically against one another absorbing the volume of the slot 38, so that the rib 26 can bite onto the pivot and reach the groove 36 in which it becomes lodged, with its face 29 butting against the shoulder 37 of the groove 36. Once the rib 26 is in abutment, the two half-sections 39 through elasticity return to their parted position and block the rib 26 in position in the groove 36. It has therefore been understood that the connecting rod 20 elastically clip fastens transversely on the transverse pivot 33a via its end 22a and finds itself blocked there in both transverse directions thanks to the collaboration of the reliefs 26, 36 which constitute means of fitting with two-way transverse blocking, so that not only does the connecting rod tend not to disengage from its pivot, but it also remains some distance away from the bite tray 11 and does not rub against the latter.

We now come to the second means of fitting, those of the posterior fixings 30p. In the embodiment depicted, the male element is on the bite tray 10 and therefore comprises the transverse pivot 33p which has a cylindrical first section 40, on the side of the bite tray 10, followed by a smaller-diameter cylindrical throat 41, itself followed by an end button or shoulder 42 of greater diameter (cf. FIG. 4). The throat 41 comprises two diametrically opposed parallel flats 43 which between them define a minimal dimension of the pivot that is intended to fit into an opening 45 in the connecting rod end 22a.

The connecting rod end 22a is in the form of an open ring, which therefore has said opening 45 between two branches 46. The dimension of the opening 45 is enough to allow the pivot 33p to pass when the pivot is offered up with its minimum dimension between the flats 43.

The fitting of the connecting rod 20 to the bite tray 10 is depicted in FIGS. 6 to 8. According to FIG. 6, the end 22p of the connecting rod 20 is brought up closer to the attachment device 30p of the bite tray 10. As the arrow in FIG. 7 shows, this moving-together takes place in the direction parallel to the two flats 43 so as to cause the opening 45 to travel along the flats 43 until the closed end of the open ring formed by the end 22p comes into abutment against the cylindrical throat 41 on which the flats 43 are formed. By then rotating the connecting rod in the direction indicated by the arrow in FIG. 8, the connecting rod pivots via the open ring on the throat 41 and finds itself, when it adopts its working position depicted in FIG. 1, in a position in which it can no longer be disengaged from the pivot, like a key that has been inserted into a lock and turned, the flats 43 being substantially perpendicular to the connecting rod in the working position. In this position, the connecting rod 20 is pivot-mounted on the pivot 33p but is blocked in both directions transversely, toward the inside by the shoulder formed between the throat 41 and the cylindrical first section 40, and toward the outside by the shoulder formed by the button 42.

Once this fitting means has been installed, the other connecting rod end 22a can easily be fitted by elastic clip-fastening onto the anterior pivots 33a and the intrabuccal device is ready for use.

By virtue of its two different means of fitting the connecting rods to the pivots in an articulated manner, the invention succeeds in overcoming, and in an effective way for a very small amount of space, the problem of the retention of the connecting rods, notably made of molded plastic, in all the situations encountered.

What is claimed is:

1. An intrabuccal device, comprising:
   a pair of bite trays;
   a first and second associated connecting rods, the connecting rods having respective first and second ends, the connecting rods being configured to be arranged in a vestibular position;
   the bite trays defining a median sagittal plane, one of the bite trays comprising at least two anterior transverse lateral fixings, the other of the bite trays comprising at least two posterior transverse lateral fixings, the lateral fixings being arranged to articulate the ends of the two connecting rods, and the ends of each connecting rod respectively laterally connecting one of the anterior transverse lateral fixings of one bite tray to one of the posterior transverse lateral fixings of the other bite tray;
   each of said transverse lateral fixings and the corresponding said first or second connecting rod end comprising means of pivot-mounting the connecting rod on the corresponding fixing with transverse blocking, one each of the anterior transverse lateral fixings or one each of the posterior transverse lateral fixings and the associated first connecting rod first ends comprising first means of fitting by elastic snap-fastening in a direction orthogonal to the median sagittal plane;
   the connecting rods second ends each comprising an open ring located and configured to receive the corresponding said anterior or posterior transverse lateral fixing in the open ring;
   another one of each of the anterior transverse lateral fixings or another one of each of the posterior transverse lateral fixings and the associated connecting rod second ends comprising second means of fitting by radial locking in an the open ring and in a plane parallel to the median sagittal plane;
   the anterior transverse lateral fixings or the posterior transverse lateral fixings respectively define a respective axis of articulation in cooperation with the associated connecting rod end which is orthogonal to the median sagittal plane;
   the direction for introduction of the connecting rod end which is an open ring over the axis of articulation of the associated transverse lateral fixing is radial, in a plane parallel to the median sagittal plane; and
   the elastic snap-fastening of the connecting rod end with the associated fixing is made according to a direction orthogonal to the median sagittal plane.

2. The device as claimed in claim 1, wherein the open ring includes an opening,
   the second means of fitting comprise a male element having an orientation in which the male element has a transverse dimension smaller than the opening of the open ring, which dimension is obtained by virtue of two diametrically opposed parallel flats formed on a generally cylindrical surface of the male element.

3. The device as claimed in claim 1, wherein the anterior and posterior transverse lateral fixings are arranged in such a way as to form, for each associated connecting rod end, an axis of pivoting that is orthogonal to the sagittal plane.

4. The device as claimed in claim 1, wherein one of the bite trays is a lower bite tray and the other of the bite trays is an upper bite tray, the first means of fitting are provided on the anterior transverse lateral fixings which are on the lower bite tray, and the second means of fitting are on the posterior transverse lateral fixings which are on the upper bite tray, the connecting rods being fitted in a propulsion set up.

5. The device as claimed in claim 1, wherein the first and the second means of fitting comprise two-way transverse stop means, for preventing the connecting rod from leaving the corresponding transverse lateral fixing and also for holding the corresponding connecting rod away from the bite trays.

6. The device as claimed in claim 1, wherein the connecting rods are made of molded semi-rigid or rigid plastic.

7. The device as claimed in claim 1, wherein the anterior and posterior transverse lateral fixings each comprise a male pivot element and the associated connecting rods each comprise a female element at their end.

8. The device as claimed hi claim 1, wherein the connecting rod has an end with a circular profile that is open over a cross section such that the connecting rod can be engaged on a throat, provided with flats, of a pivot formed on the posterior fixing.

9. An intrabuccal device comprising:
- an upper bite tray, and a lower bite tray positioned below the upper bite tray; the bite trays defining a median sagittal plane;
- one of the bite trays having two opposite lateral sides, each lateral side of the one bite tray including a respective anterior lateral fixing;
- the other of the bite trays also having two opposite lateral sides, each lateral side of the other bite tray including a respective posterior lateral fixing which is posterior to the anterior lateral fixings on the one bite tray;
- a first and a second connecting rod, each connecting rod being configured to be arranged in a vestibular position, each of the first and second connecting rods being at a respective one of the two opposite lateral sides of both of the bite trays;
- each connecting rod having respective opposite ends, one of the ends of each of the first and second connecting rods respectively connecting to the anterior transverse lateral fixing at a respective one of the opposite lateral sides of the one of the bite trays, the other of the ends of each of the first and second connecting rods respectively connecting to the posterior transverse lateral fixing at a respective one of the opposite lateral sides of the other of the bite trays, whereby each of the anterior and posterior fixings on each bite tray is connected with a respective opposite end of one of the first and second connecting rods;
- one each of the anterior transverse lateral fixings or one each of the posterior transverse lateral fixings and the associated first connecting rod ends comprising first means of fitting by elastic snap-fastening in a direction orthogonal to the median sagittal plane;
- the second connecting rod ends are each shaped as an open ring in a plane parallel to the median sagittal plane;
- another one of each of the anterior transverse lateral fixings or another one of each of the posterior transverse lateral fixings and the associated second connecting rod ends comprise second means of fitting by radial locking of the respective fixing in the open ring, in a plane parallel to the median sagittal plane;
- the anterior fixings on one of the bite trays and the posterior fixings on the other of the bite trays each define an axis of articulation in cooperation with the associated connecting rod end which is orthogonal to the median sagittal plane;
- a direction for introduction of the connecting rod end which is shaped as an open ring through the opening in the open ring and over the axis of articulation of the associated transverse lateral fixing is radial, in a plane parallel to the median sagittal plane; and
- the elastic snap-fastening of the connecting rod end with the associated fixing is made according to a direction orthogonal to the median sagittal plane.

10. The device of claim 9, wherein the anterior transverse lateral fixings are on the lower bite tray and the posterior transverse lateral fixings are on the upper bite tray and, the anterior transverse lateral fixings are located on the lower bite tray forward on the bite trays of the posterior transverse lateral fixings on the upper bite tray.

* * * * *